(12) United States Patent
Takada et al.

(10) Patent No.: US 10,989,632 B2
(45) Date of Patent: Apr. 27, 2021

(54) METHOD FOR PREPARING STANDARD SAMPLE FOR GAS FLOW TYPE ANALYSIS SYSTEM

(71) Applicant: Hitachi, Ltd., Tokyo (JP)

(72) Inventors: Yasuaki Takada, Tokyo (JP); Shun Kumano, Tokyo (JP); Masuyuki Sugiyama, Tokyo (JP); Hisashi Nagano, Tokyo (JP); Tatsuo Nojiri, Tokyo (JP); Hiroki Mizuno, Tokyo (JP); Yuichiro Hashimoto, Berkshire (GB)

(73) Assignee: Hitachi, Ltd., Tokyo (JP)

( * ) Notice: Subject to any disclaimer, the term of this patent is extended or adjusted under 35 U.S.C. 154(b) by 376 days.

(21) Appl. No.: 15/822,780

(22) Filed: Nov. 27, 2017

(65) Prior Publication Data

US 2018/0149563 A1     May 31, 2018

(30) Foreign Application Priority Data

Nov. 29, 2016 (JP) .............................. JP2016-231763

(51) Int. Cl.

| | |
|---|---|
| *G01N 1/38* | (2006.01) |
| *G01N 1/40* | (2006.01) |
| *G01N 1/36* | (2006.01) |
| *G01N 33/00* | (2006.01) |
| *G01N 1/28* | (2006.01) |
| *G01N 1/02* | (2006.01) |
| *G01N 35/00* | (2006.01) |

(52) U.S. Cl.
CPC ................. *G01N 1/38* (2013.01); *G01N 1/28* (2013.01); *G01N 1/36* (2013.01); *G01N 1/40* (2013.01); *G01N 33/0011* (2013.01); *G01N 2001/022* (2013.01); *G01N 2001/2893* (2013.01); *G01N 2035/00188* (2013.01)

(58) Field of Classification Search
CPC .. G01N 1/38; G01N 1/40; G01N 1/36; G01N 33/00
USPC ........................................................ 436/8, 179
See application file for complete search history.

(56) References Cited

U.S. PATENT DOCUMENTS 5,741,984 A * 4/1998 Danylewych-May ....................... A61B 10/0096
73/864
6,470,730 B1  10/2002 Chamberlain
(Continued)

FOREIGN PATENT DOCUMENTS

| | | |
|---|---|---|
| CN | 103293266 A | 9/2013 |
| DE | 41 31 251 A1 | 4/1993 |

(Continued)

OTHER PUBLICATIONS

Sigman, M. E. et al, Analytical Chemistry 1999, 71, 4119-4124.*
(Continued)

*Primary Examiner* — Arlen Soderquist
(74) *Attorney, Agent, or Firm* — Crowell & Moring LLP

(57) ABSTRACT

An object of the invention is to improve uniformity of a standard sample used for evaluating a gas flow type analysis system. The invention includes weighing a background into a container; adding a sample solution to the background; drying the sample solution; adding a solvent that can dissolve the sample into the container; and drying the solvent added to the container. The invention is also characterized in that the solvent is an organic solvent, in particular, acetone.

2 Claims, 9 Drawing Sheets

(56) References Cited

U.S. PATENT DOCUMENTS

| | | | | |
|---|---|---|---|---|
| 7,161,144 | B2* | 1/2007 | Syage | H01J 49/04 250/285 |
| 9,200,992 | B2* | 12/2015 | Danylewych-May | G01N 1/02 |
| 2003/0155500 | A1* | 8/2003 | Syage | H01J 49/04 250/281 |
| 2004/0014233 | A1* | 1/2004 | Bannister | G01N 25/4866 436/155 |
| 2006/0154234 | A1* | 7/2006 | Winther | G01N 1/36 435/4 |
| 2006/0192098 | A1* | 8/2006 | Danylewych-May | G01N 1/02 250/281 |
| 2009/0107593 | A1* | 4/2009 | Lee | C06B 21/0066 149/2 |
| 2011/0186436 | A1* | 8/2011 | Novosselov | B01D 15/08 204/600 |
| 2011/0203931 | A1* | 8/2011 | Novosselov | G01N 1/2202 204/600 |
| 2013/0130398 | A1* | 5/2013 | Zang | G01N 21/78 436/128 |
| 2014/0097551 | A1* | 4/2014 | Vu | C06B 23/00 264/3.4 |
| 2014/0127824 | A1* | 5/2014 | Amisar | G01N 21/78 436/107 |
| 2014/0151543 | A1 | 6/2014 | Nagano et al. | |
| 2014/0238106 | A1 | 8/2014 | Kashima et al. | |
| 2015/0198727 | A1 | 7/2015 | Ingham et al. | |

FOREIGN PATENT DOCUMENTS

| | | |
|---|---|---|
| EP | 0 655 618 A2 | 5/1995 |
| EP | 2 894 463 A1 | 7/2015 |
| JP | H 11-190685 | 7/1999 |
| JP | 2009-31072 A | 2/2009 |
| JP | 2013-83472 A | 5/2013 |
| JP | 5690840 B2 | 3/2015 |
| JP | 2015-132607 A | 7/2015 |

OTHER PUBLICATIONS

Fletcher, R. A. et al, Talant 2008, 76, 949-955.*
MacCrehan, W. A, Analytical Chemistry 2009, 81, 7189-7196.*
MacCrehan, W. A, Analytical Chemistry 2011, 83, 9054-9059.*
Hashimoto, Y. et al, Rapid Communications in Mass Spectrometry 2014, 28, 1376-1380.*
Takada, Y. et al, IEEE Sensors Journal 2016, 16, 1119-1129.*
"Standard Practice for Measuring and Scoring Performance of Trace Explosive Chemical Detectors", ASTM International, Designation: E2520-15, Feb. 2015, pp. 1-9.
European Search Report issued in counterpart European Application No. 17204018.0 dated Apr. 26, 2018 (twelve (12) pages).
Japanese-language Office Action issued in Japanese Application No. 2016-231763 dated Feb. 18, 2020 with English translation (11 pages).
Kimura et al., "Development of Powdered Polyethylene Reference Materials for X-Ray Fluorescence Analysis of Hazardous Elements", Analytical Chemistry, 2008, pp. 411-415, vol. 57, No. 6, with English abstract (six (6) pages).
"Powder for JIS Z 8901 test for Japan powder industrial Technology", Japan Powder Industrial Engineering Association, Jan. 6, 2010, pp. 1-51 with partial English translation (52 pages).

* cited by examiner

METHOD FOR PREPARING STANDARD SAMPLE FOR GAS FLOW TYPE ANALYSIS SYSTEM

FIELD OF INVENTION

The present invention relates to a method for preparing a standard sample for a gas flow type analysis system for evaluating a gas flow type analysis system that analyzes an attached substance attached to a test subject.

BACKGROUND ART

It has become important to detect substances such as an explosive at an entrance of an airport, an amusement park, and other facilities. It is known on handling such a dangerous substance as an explosive that particulates derived from the dangerous substance scatter to the periphery. Accordingly, when particulates from a dangerous substance such as an explosive are attached to a test subject (for example, a hand, a cloth, a bag, or the like), a person relating to the test subject has highly possibly handled the dangerous substance. Thus, an analysis system for rapidly analyzing particulates attached to a test subject is becoming increasingly important.

PTL 1 discloses an analysis device and an analysis method "characterized by including: a gas feeding unit for peeling off a sample attached to a subject; a gas sucking unit for sucking the sample peeled off from the subject; a particulate capturing unit that includes a conical particulate concentrating unit, and concentrates and captures the sucked sample; a large capacity sucking unit provided above the particulates concentrating unit; a particulate capturing filter provided in a small radius part of the particulate concentrating unit; a heating unit for heating the particulate capturing filter provided in the small radius part of the particulate concentrating unit; a small capacity sucking unit for continuously sucking a sample, which has been captured by the particulate capturing filter and vaporized by the heating, from the back surface of the particulate capturing filter; an ion source unit in which the sucked sample is introduced and ionized; a mass analysis unit for analyzing the masses of ions produced in the ion source unit; a controlling unit that controls the ion source unit and the mass analyzing unit; a database unit that stores mass spectrum data derived from a substance to be detected; and a determining unit that collates the result of the mass analysis of the sample by the mass analyzing unit with the mass spectrum data stored in the database unit to determine the presence or absence of the substance to be detected" (see, claim 1).

In order to correctly evaluate the performance for an attached substance in such an analysis system (analysis device), it is necessary to establish a preparation method of a standard sample to be used in a test of the analysis system and an evaluation procedure of the analysis system. PTL 2 discloses a method for preparing a standard sample used for evaluating an analysis system, in which a sample solution is added dropwise on a Teflon sheet and dried, and a precipitated sample is rubbed against a test subject, thereby attaching a desired sample on the test subject.

In addition, NPL 1 establishes a specification of a preparation method of a standard sample used for evaluating an analysis system and an evaluation procedure thereof. Specifically, a procedure is described in which a background suspension is added dropwise on a commercially available paper waste, followed by drying, then a sample solution is added dropwise on the same paper waste, followed by drying, and the paper waste containing desire amounts of the background and the sample is tested by the analysis system.

CITATION LIST

Patent Literatures

PTL 1: Japanese Patent No. 5690840
PTL 2: USP 6470730

Non-Patent Literature

NPL 1: ASTM Standard E2520-15 (ASTM International)

SUMMARY OF INVENTION

Technical Problem

PTL 2 and NPL 1 describe a preparation method of a standard sample and an evaluation procedure which are basically used in a so-called wiping inspection type analysis system in which a surface of a test subject is wiped with a commercially available paper waste and then particulates attached to the paper waste are analyzed. Thus, there are no preparation method of a standard sample and no evaluation procedure that are suitable for a gas flow type analysis system as shown in PTL 1, in which an attached substance attached to a surface of a test subject is collected by a gas flow without wiping and analyzed.

In addition, in a step for attaching particulates on a test subject, if a sample solution is directly added dropwise onto the test subject and dried, the test subject is possibly melted depending on the material of the test subject or the kind of the solvent in the sample solution. Furthermore, if the test subject is a hand, a sample solution may be unsuitable for human skin.

The present invention has been made in view of the above circumstance, and the present invention has an object to improve uniformity of a standard sample used for evaluating a gas flow type analysis system.

Solution to Problems

For solving the above problem, the present invention is characterized by including the steps of: weighing a background into a container; adding a solution of a sample to the background; drying the solution of the sample; adding a solvent that can dissolve the sample into the container; and drying the solvent added into the container.

Other resolutions will be described in embodiments.

Advantageous Effects of Invention

According to the present invention, uniformity of a standard sample used for evaluating a gas flow type analysis system can be improved.

DESCRIPTION OF EMBODIMENTS

Figure 1:
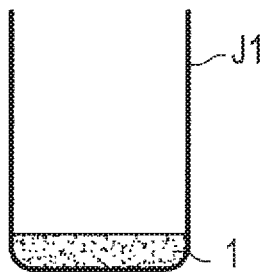
FIG. 1 is a diagram (No. 1) showing a preparation method of a standard sample used in a first embodiment.

Next, modes for implementing the present invention (referred to as "embodiments") will be described in detail with reference to drawings as needed. Here, a plastic card is first taken as a test subject, and an evaluation method of a gas flow type analysis system in which particulates attached to the card surface are sampled by a gas flow and analyzed is explained.

In the drawings, an identical sign is assigned to elements having an identical configuration, and the explanation is omitted.

First Embodiment

First, referring to FIG. 1 to FIG. 8, a preparation method of a standard sample used in a first embodiment will be explained.

As shown in FIG. 1, a background 1 is first weighed into a container J1. The background 1 is particulates that are highly possibly (possibly) attached to a test subject at the time of performing a test by an analysis system, specifically dust or the like. The background 1 is desirably a powder having a known particle size and a known composition. For example, as the background 1, the test powder (fine) Class 7 Kanto (Japanese) loam for JIS Z8901, specified by JIS (Japanese Industrial Standard), or the like is desirably used. As the container J1, a glass container whose content is easily viewed is desirably used, but a resin container may be used.

Figure 2:
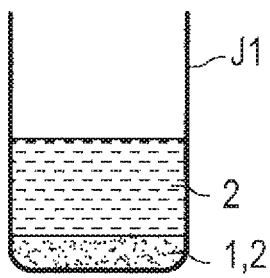
FIG. 2 is a diagram (No. 2) showing the preparation method of a standard sample used in the first embodiment.

Next, as shown in FIG. 2, a sample solution (a solution of a sample) 2 is added into the container J1 so as to give a desired concentration (wt %) of the sample (an explosive, herein) relative to the background 1 in the container J1. The sample solution 2 is a substance to be subjected to an analysis, and if an explosive is used for a test of a gas flow type analysis system w (see, FIG. 9), the explosive is the sample. At this time, on the bottom of the container J1, the background 1 impregnated with the sample solution 2 gathers.

Figure 3:
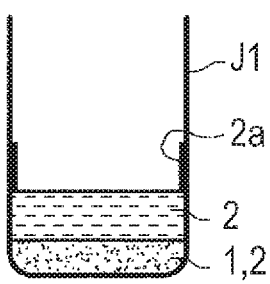
FIG. 3 is a diagram (No. 3) showing the preparation method of a standard sample used in the first embodiment.
Figure 4:
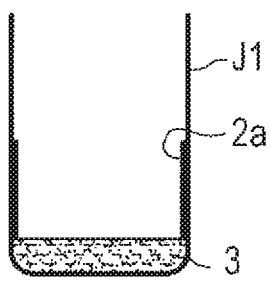
FIG. 4 is a diagram (No. 4) showing the preparation method of a standard sample used in the first embodiment.

Then, as shown in FIG. 3 and FIG. 4, the container J1 in which the sample solution 2 is added to the background 1 is placed in a draft chamber and a solvent 4 is dried. In this manner, a standard sample 3 containing the sample (the explosive, herein) is prepared. (see FIG. 4). In techniques in the related art, preparation of the standard sample 3 has been completed at the stage of FIG. 4.

However, according to the study of the present inventors, when the gas flow type analysis system w (see FIG. 9) was evaluated with the standard sample 3 in the state of FIG. 4, the reproducibility was found to be poor even though the standard sample 3 was sufficiently peeled off from the test subject.

A cause thereof is considered as follows: when the sample solution 2 is added into the container J1 and the solvent 4 is dried, as shown in FIG. 3 and FIG. 4, a part of a precipitated sample 2a is left on an inner wall surface and the like of the container J1 and is not mixed uniformly with the background 1.

Figure 5:
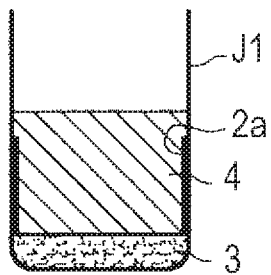
FIG. 5 is a diagram (No. 5) showing the preparation method of a standard sample used in the first embodiment.

Thus, in the first embodiment, an appropriate amount of the solvent 4 is added to the standard sample 3 containing the sample once dried in the container J1, as shown in FIG. 5. The solvent 4 added is one having a strong affinity to the sample (explosive). In the "appropriate amount", it is desired that the liquid surface of the solvent 4 IS higher than the level of the sample 2a left on the wall surface of the container J1. By the solvent 4, the sample 2a left on the wall surface of the container J1 and the sample 2a on the surface of the background 1 are re-dissolved in the solvent 4. Thus, the sample 2a left on the wall surface of the container J1 is rinsed (washed). Here, the solvent 4 to be used for the re-dissolution of the sample 2a is desirably an organic solvent, particularly acetone. Acetone dissolves well a chemical substance such as an explosive and in addition has a high vapor pressure, being dried easily.

Figure 6:
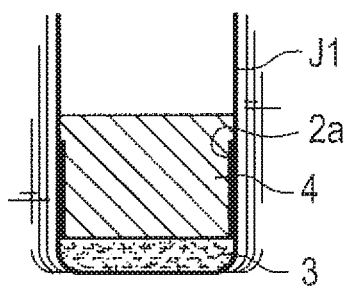
FIG. 6 is a diagram (No. 6) showing the preparation method of a standard sample used in the first embodiment.
Figure 7:
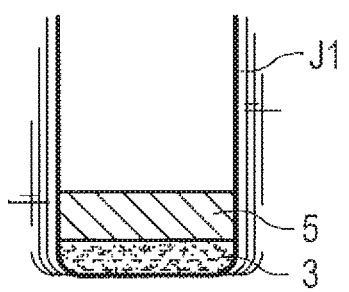
FIG. 7 is a diagram (No. 7) showing the preparation method of a standard sample used in the first embodiment.

Then, as shown in FIG. 6 and FIG. 7, the solvent 4 is dried. As described above, the solvent 4 has a strong affinity to the sample, and therefore even when the solvent 4 is dried to reduce the amount of the solvent 4 in the container J1, the sample remains dissolved in the solvent 4. In other words, since the sample is dissolved in the solvent rather than left on the wall surface, even when the solvent 4 is gradually dried, the sample does not remain on the wall surface.

Incidentally, when the solvent 4 is dried, as shown in FIG. 6 and FIG. 7, the solvent 4 may preferably be dried by stirring with a vibration stirrer and the like. Incidentally, when the container J1 is stirred with a vibration stirrer or the like, the solvent 4, the standard sample 3, and the sample 2a become in a mixed state. In FIG. 6 and FIG. 7, however for the sake of understandability, the solvent 4, the standard sample 3, and the sample 2a are illustrated in a separated state.

Figure 8:
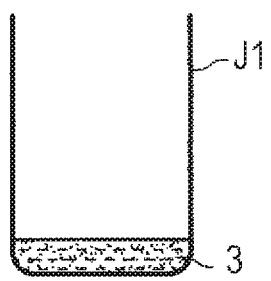
FIG. 8 is a diagram (No. 8) showing the preparation method of a standard sample used in the first embodiment.

As shown in FIG. 8, when the solvent 4 is dried completely, the standard sample 3 for evaluation in which the background 1 and the sample are uniformed mixed remains on the bottom of the container J1.

Here, after (trying the solvent 4, the standard sample 3 in the container J1 is in a solidified state, the solid is broken into particles with a needle or the like before use.

(Gas Flow Type Analysis System)

Figure 9:
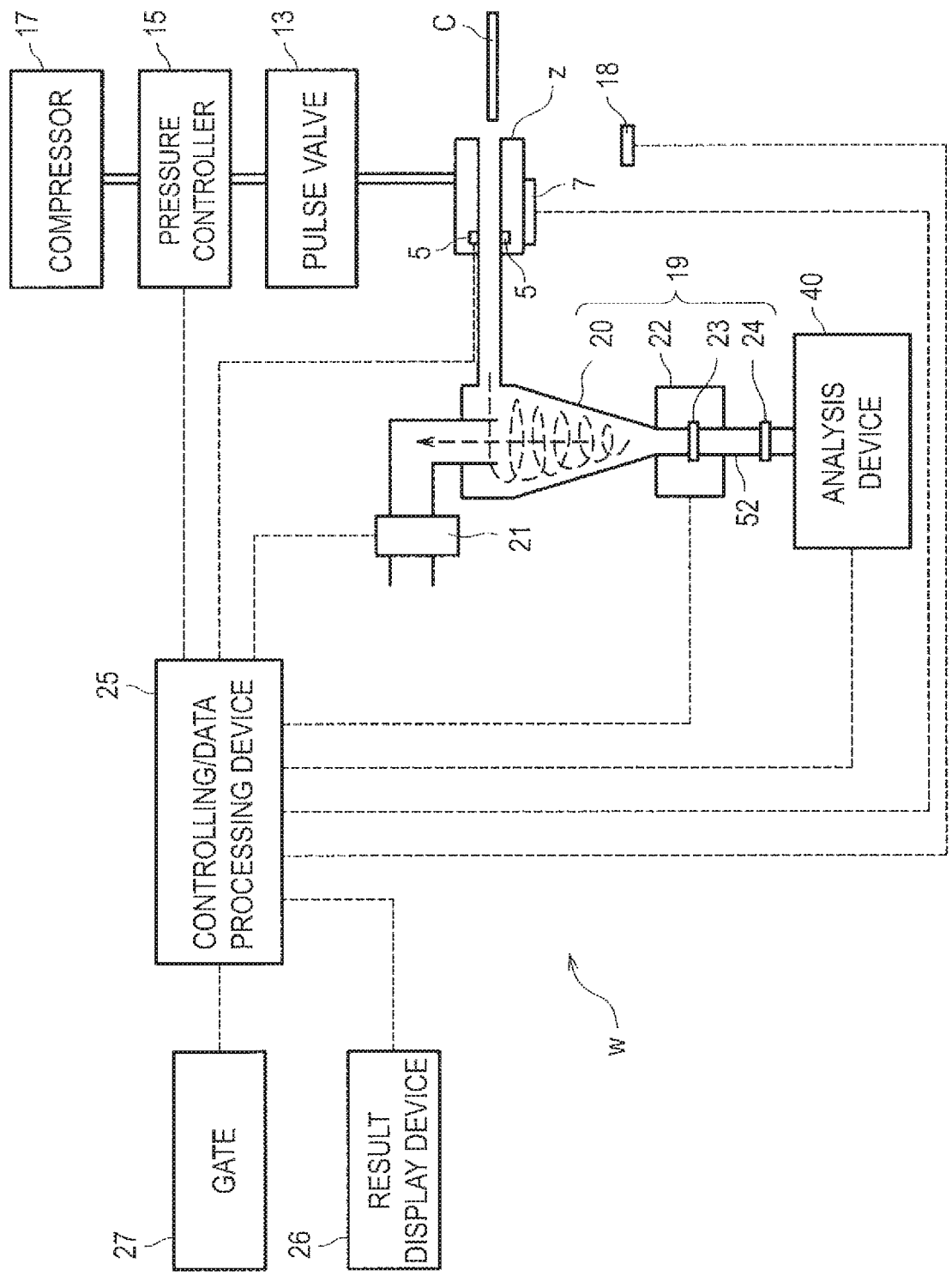
FIG. 9 is a diagram showing an example of a gas flow type analysis system to be evaluated by a standard sample.

FIG. 9 is a diagram showing an example of a gas flow type analysis system to be evaluated by a standard sample. A standard sample prepared in the first embodiment or in the second or third embodiments described later is used for evaluation of the gas flow type analysis system w as shown in FIGS. 9 to 12.

The gas flow type analysis system w is assumed to be a security gate system that is capable of performing analysis of an attached substance attached to a surface of a test subject C and authorization of the test subject C. In particular, the system is intended to detect a dangerous substance such as an explosive. The gas flow type analysis system w includes an attached substance collection device z, an authorization device 7, an infrared sensor 5, a pulse valve 13, a pressure controller 15, a compressor 17, a human detection sensor 18, and an attached substance concentrating device 19. The gas flow type analysis system w further includes an analysis device 40, a gas suction device 21, a controlling/data processing device 25, a result display device 26, and a gate 27. As the human detection sensor 18, an infrared sensor and an ultrasonic sensor are applicable.

In addition, the attached substance concentrating device 19 includes a cyclone capturing unit 20, a heater 22, a primary filter 23, and a secondary filter 24. Incidentally, the gas flow type analysis system w is not necessarily limited to the configuration shown in FIG. 9, and FIG. 9 merely illustrates a typical example.

The attached substance concentrating device 19 increases a concentration of the attached substance peeled off.

The cyclone capturing unit 20 is capable of capturing a sample having fixed levels or larger of the particle size and density into a lower portion of the cyclone capturing unit 20 by means of centrifugal force.

The attached substance captured in the lower portion of the cyclone capturing unit 20 settles as it is onto the heater 22. The heater 22 is provided with the primary filter 23. The attached substance settled is captured by the primary filter 23 and heated by the heater 22, thereby vaporizing. The attached substance vaporized passes through the secondary filter 24 and is introduced into the analysis device 40. The attached substance concentrating device 19 is only required to concentrate the attached substance peeled off and does not have to be provided with the cyclone capturing unit 20.

The heater 22 heats the attached substance, for example, to 200° C. The temperature of the heater 22 is only required to be a temperature at which the attached substance to be captured can be vaporized and may be varied depending on the component in the attached substance.

The primary filter 23 and the secondary filter 24 are only required to have a filter rating that can capture particulates of 1 µm or larger. A pipe 52 connecting the heater 22 and the analysis device 40 is also heated. This is for preventing adsorption of the molecules vaporized by the heater 22 on an inner wall of the pipe 52. The secondary filter 24 is placed for the purpose of preventing the attached substance that has not been captured on the primary filter 23 from entering the analysis device 40. The pipe 52 between the heater 22 and the analysis device 40 is not necessarily required, and the heater 22 and the analysis device 40 may be directly connected. In this case, the secondary filter 24 is omitted.

As the analysis device 40, a mass spectrometer is used.

When a mass spectrometry apparatus is used as the analysis device 40, the controlling/data processing device 25 analyzes a mass spectrum measured by the analysis device 40 to identify the component of the attached substance and to specify the concentration thereof based on the mass spectrum. In the controlling/data processing device 25, a database is previously stored. In the database, a threshold for identifying the component of the attached substance or determining the concentration thereof is set. When a concentration of a detected component exceeds the defined threshold, the controlling/data processing device 25 effects a positive determination. Then, the result display device 26 displays the presence or absence of the detected component, and the like.

Incidentally, the dotted line in FIG. 9 shows a transmission and reception of information. As shown in FIG. 9, the controlling/data processing device 25 acquires information from the infrared sensor 5, the authorization device 7, the human detection sensor 18, and the analysis device 40. In addition, the controlling/data processing device 25 controls the pressure controller 15, the heater 22, the gate 27, the gas suction device 21, and the like based on the acquired information. In addition, the controlling/data processing device 25 causes the result display device 26 to display the analytical result in the analysis device 40, and the like.

The controlling/data processing device 25 closes the gate 22 when an explosive is detected.

(Attached Substance Collection Device)

Figure 10:
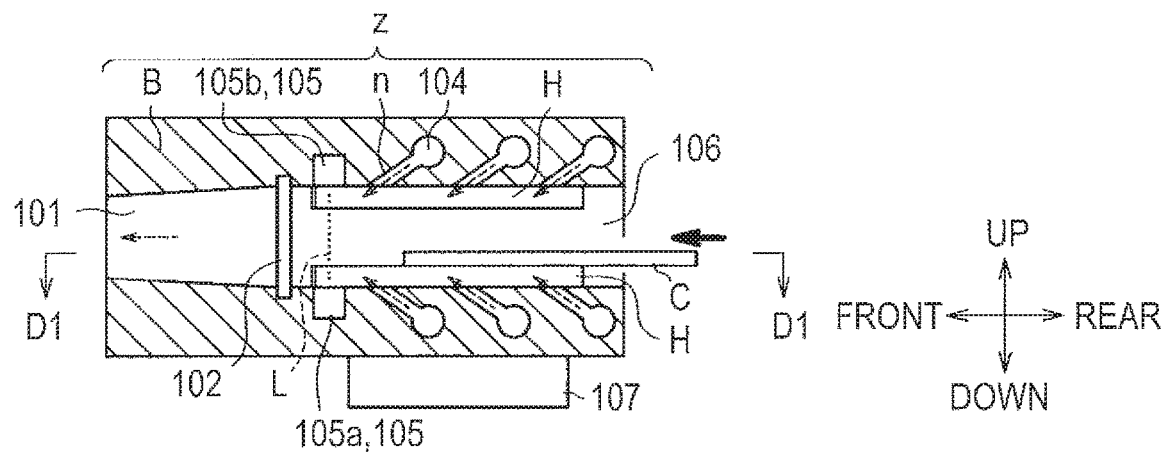
FIG. 10 is a diagram showing a schematic cross section of an attached substance collection device.
Figure 11:
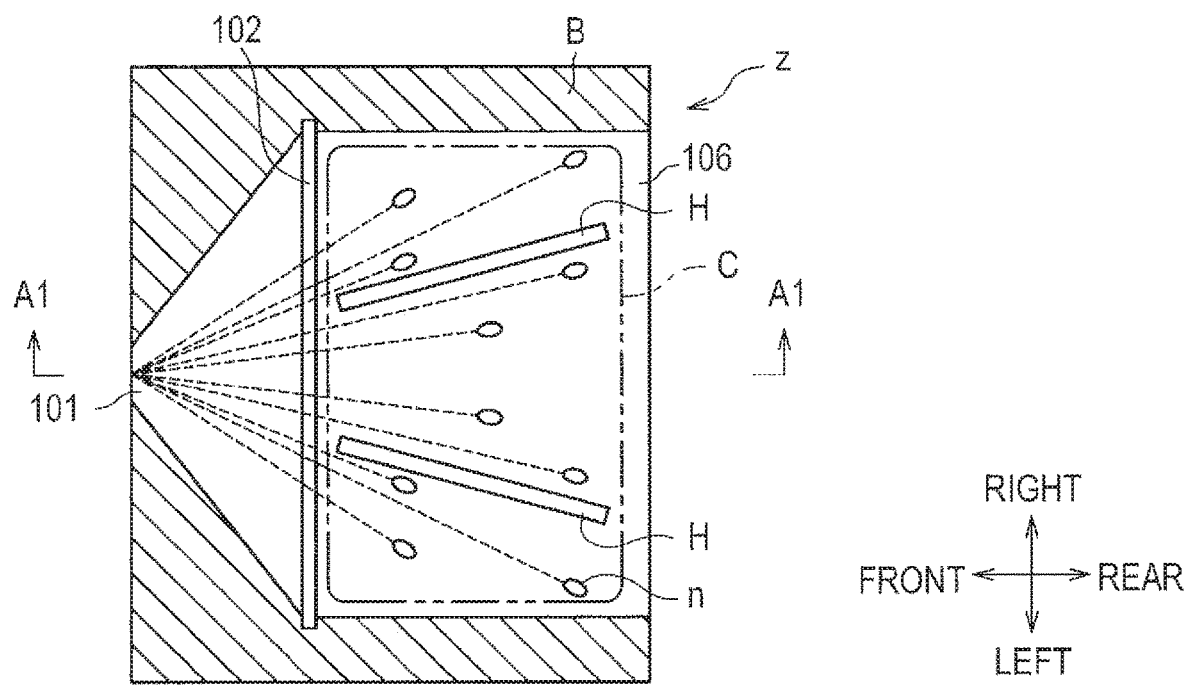
FIG. 11 is a diagram showing a positional relation of spouting nozzles, a test subject, supports, and a collection port of an attached substance collection device viewed from above.
Figure 12:
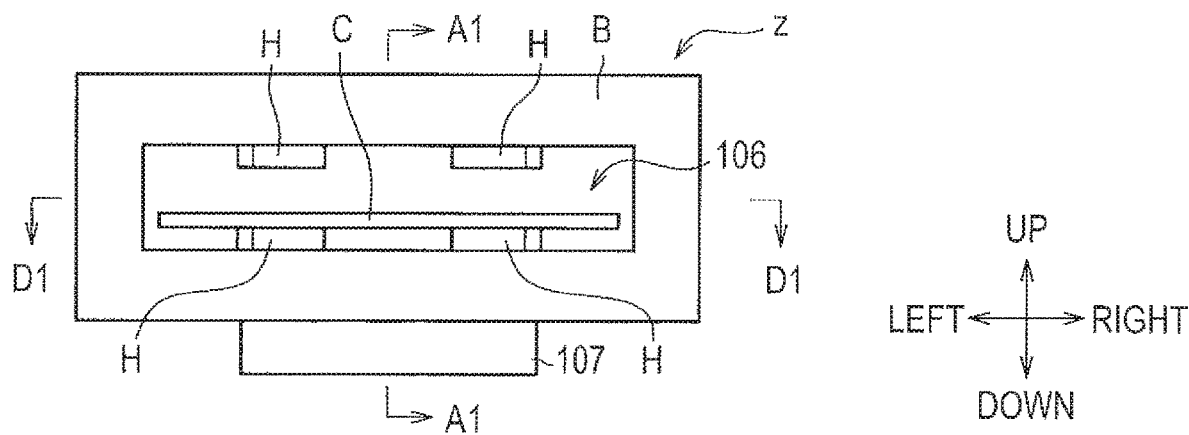
FIG. 12 is a diagram of an attached substance collection device viewed from an insertion port side of a test subject.

FIG. 10 is a diagram showing a schematic cross section of the attached substance collection device. FIG. 11 is a diagram showing a positional relation of spouting nozzles, test subject, supports, and a collection port of the attached substance collection device illustrated in FIG. 10 viewed from above. FIG. 12 is a diagram of the attached substance collection device illustrated in FIG. 10 viewed from an insertion port side of a test subject.

Incidentally, FIG. 10 shows an A1-A1 cross section in FIG. 11 and FIG. 12, and FIG. 11 shows a D1-D1 cross section in FIG. 10 and FIG. 12. Nozzles n is actually hidden behind a housing B, but in FIG. 10, they are illustrated as the cross sections for the conceptual understandability. Furthermore, in FIG. 10, although five nozzles n are actually to be illustrated, only three nozzles are shown for avoiding complication of the drawing. The same is true in the drawings mentioned below.

FIG. 10 and FIG. 11 show a state where the test subject (subject) C is on its way of insertion. Also in the drawings mentioned below, similar drawings show a state where the test subject C is on its way of insertion.

As shown in FIG. 10 and FIG. 12, an attached substance collection device z is provided with a pair of supports spacers) H on each of the upper and lower surface of an interior space where the spouting nozzles n are disposed. The supports H have a protrusion structure, that is, a rib shape.

In addition, the gas flow type analysis system w in the first embodiment (see FIG. 9) jets a gas flow (gas) against both the surfaces of the test subject C, such as, for example, an IC (integrated circuit) card and a magnetic card in order to collect an attached substance attached to the test subject C. In addition, the gas flow type analysis system w performs authorization when the test subject C is inserted into the attached substance collection device z and acquires the authorization data. Incidentally, the authorization data are written on an IC chip, a magnetic medium, a bar code, or a two dimensional code that is embedded in the test subject C, attached to a surface thereof, or printed thereon.

Then, the gas flow type analysis system w performs authorization of the test subject C based on the authorization data.

In this time, the positional relation between the spouting nozzles n, which are jetting ports for jetting a gas flow, and the test subject C is constant for each test by the supports H disposed in the attached substance collection device z. This makes it possible to stably collect the attaches substance attached on the test subject C. The height of the supports H is desirably approximately from 2 to 3 mm.

As shown FIG. 11, in the attached substance collection device z according to the embodiment, ten spouting nozzles n are disposed on the lower surface of the interior space of the housing B. Since the spouting nozzles n are disposed on the upper and lower surfaces of the interior space of the housing B, twenty spouting nozzles n are used in total in this embodiment.

In this embodiment, as the test subject. C, an IC card, a magnetic card, a name card, a card holder capable of holding such a card, and the like are assumed, but the test subject C is not limited thereto. For example, a cell phone, a portable terminal, a ticket, a passport, and the like can be applied.

In this embodiment, as shown in FIG. 10, when the test subject C is inserted in the internal space formed by the housing B, jet of a gas flow from the spouting nozzles n is started, and a test is thus started. By the gas flow jetted from the spouting nozzles n, the attached substance can be peeled off and collected from both the upper and lower surfaces of the test subject C.

Here, the dotted line arrow shown in the FIG. 10 and the dotted lines shown in FIG. 11 show the gas flow. In addition, a bold solid line arrow shown in FIG. 10 shows the insertion direction of the test subject C.

As shown in FIG. 10 and FIG. 11, the gas flow jetted from the spouting nozzles n collides to the test subject C and then flows toward a collection port 101.

Here, by covering with the housing B the periphery of the test subject C except for the insertion port 106 for inserting the test subject C and the collection port 101 for collecting the attached substance peeled off, the attached substance peeled off can be efficiently collected from the collection port 101 without scattering outside.

As shown in FIG. 10, the spouting nozzles n are inclined relative to the vertical direction. The angle is generally in the range of approximately from 15 to 90° relative to the vertical direction (90° C. means they are vertical to the test subject C), and desirably in the range of 30 to 45°.

As shown in FIG. 10 and FIG. 12, in this embodiment, an authorization device 107 is disposed under the housing B of the attached substance collection device z. When the test subject C is, for example, an IC card, the content of the IC card is authorized by the authorization device 107.

As shown in FIG. 10, the attached substance collection device z is provided with an infrared sensor 105. The infrared sensor 105 is composed of an infrared sensor light emitter 105a and an infrared sensor light receiver 105b. The dotted line L shows an infrared ray emitted from the infrared sensor light emitter 105a. When the test subject C is inserted into the attached substance collection device z and interrupts the infrared ray L, the infrared sensor light receiver 105b detects the interruption of the infrared ray L. Thus, the insertion of the test subject C is detected.

As shown in FIG. 10 and FIG. 11, a rough mesh filter 102 is provided before the collection port 101. The rough mesh filter 102 is for preventing dust of a large particle size from entering the collection port 101. As the rough mesh filter 102, for example, a stainless steel mesh (aperture 0.5 mm, open porosity 50%) is used. The rough mesh filter 102 is exchangeable, and when clogged with dust, the rough mesh filter may be cleaned and reused, or replaced with a new product.

As shown in FIG. 10, each of the spouting nozzles n is connected to a pipe 104 for the spouting nozzle n that feeds a gas flow to the spouting nozzle n. The pipe 104 is connected to a gas flow source (described later) outside the housing B. Incidentally, in FIG. 10, the pipe 104 extends towards the front direction of the paper.

Incidentally, the subject to be evaluated by the standard sample 3 (see FIG. 8) is not limited to one having the configuration illustrated in FIG. 9 to FIG. 12 as long as it collects an attached substance on the test subject C by a gas flow and analyzes the substance.

(Effects)

Figure 13:
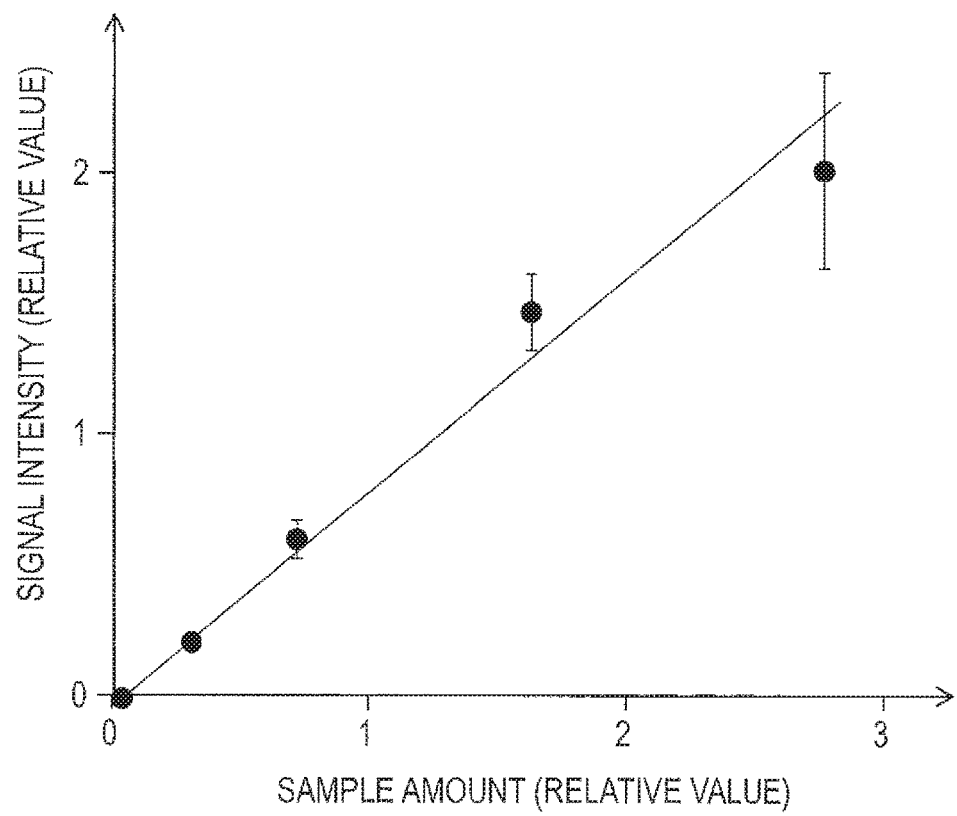
FIG. 13 is a graph showing an effect of a standard sample prepared by a technique shown in the first embodiment.

FIG. 13 is a graph showing an effect of a standard sample prepared by the technique shown in the first embodiment.

FIG. 13 shows, with a certain explosive taken as a sample, a relation between an amount of the sample contained in a standard sample attached to a test subject and a signal intensity in a case where the test subject is tested by the gas flow type analysis system w illustrated in FIG. 9 to FIG. 12.

Figure 14:
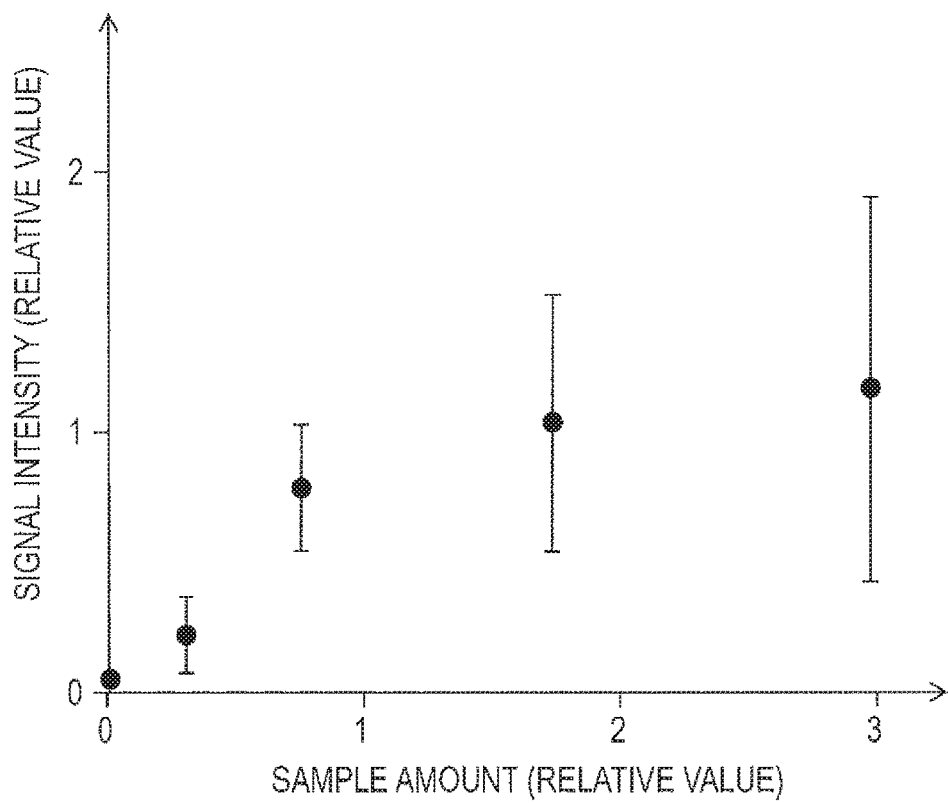
FIG. 14 is a graph showing a result of a comparative example.

FIG. 14 is a graph showing a result of a comparative example in which a similar test as in FIG. 13 was conducted using a standard sample obtained using the same substance as in FIG. 13 as a raw material without the step of washing with acetone (see FIG. 5 to FIG. 7).

As is apparent in comparison between FIG. 13 and FIG. 14, FIG. 13 in which a standard sample was prepared in a technique of the first embodiment shows a clearer correlation between the amount of the sample and the signal intensity. Thus, the use of a standard sample prepared by the technique shown in the first embodiment makes it possible to enhance the accuracy in the quantitative evaluation of the performance of the gas flow type analysis system w (see FIG. 9) of a type in which particulates are sampled by a gas flow.

The standard sample 3 prepared by the technique shown in the first embodiment is significantly increased in uniformity as compared with the standard sample 3 prepared by the technique in the related art, and an evaluation of the gas flow type analysis system w (see FIG. 9) can be performed with high accuracy.

In addition, as described above, in the method in the related art in which the solvent 4 is not added, the sample 2a is left on a wall surface of the container J1 as shown in FIG. 4. Accordingly, it is unclear what proportion of the sample added to the background 1 at the time of FIG. 2 is contained in the background 1.

In contrast, according to the method shown in the first embodiment, almost all the added sample is contained in the background 1, making it possible to accurately grasp the amount of the sample in the background 1.

Thus, the standard sample 3 produced by the technique of the first embodiment can evaluate the performance of the gas flow type analysis system w with high reproducibility, in the gas flow type analysis system w (see FIG. 9) of a type in which particulates are sampled from a test subject by a gas flow. Accordingly, the evaluation result can be used as a guideline for enhancing the performance of the gas flow type analysis system w, and therefore the technical development is promoted. In addition, it becomes possible to accurately compare different device models in performance, and a user can select a model of the gas flow type analysis system w by referring to the evaluation result when introducing the system.

Furthermore, in the first embodiment, by using an organic solvent as the solvent 4 which is added in FIG. 5, it is possible to re-dissolve the sample 2a left on a wall surface of the container J1 to prevent the sample 2a from remaining on the wall surface of the container J1 when the solvent 4 is further dried. This makes it possible to prepare the standard sample 3 with high uniformity. Furthermore, by using as the solvent 4 acetone which has particularly high affinity with the sample, it is possible to prevent the sample 2a from remaining on a wall surface of the container J1 when the solvent 4 is dried.

Second Embodiment

Next, referring to FIG. 15 to FIG. 18, the preparation method of the standard sample 3 used in the second embodiment of the present invention will be explained.

Figure 15:
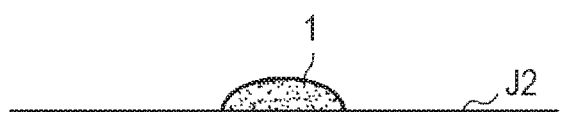
FIG. 15 is a diagram (No. 1) showing a preparation method of standard sample used in a second embodiment.

First, as shown in FIG. 15, on a Teflon sheet (sheet-like substance) a desired amount of a suspension of the background 1 prepared by the same method as in NPL 1 is added dropwise and dried. The suspension is desirably an isopropanol suspension.

Figure 16:
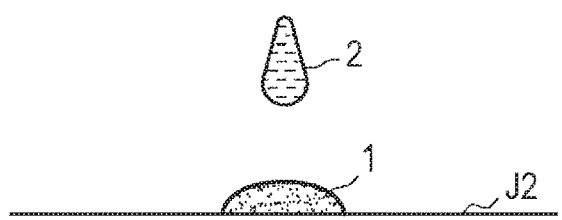
FIG. 16 is a diagram (No. 2) showing the preparation method of a standard sample used in the second embodiment.

Next, as shown in FIG. 16, a desired amount of the sample solution 2 is added dropwise with a micro-syringe and the like to the background 1 precipitated as a result of the drying. As a result, a mixture of the background 1 and the sample solution 2 is produced.

Figure 17:
FIG. 17 is a diagram (No. 3) showing the preparation method of a standard sample used in the second embodiment.

Then, as shown in FIG. 17, the mixture of the background 1 and the sample solution 2 is dried.

Figure 18:
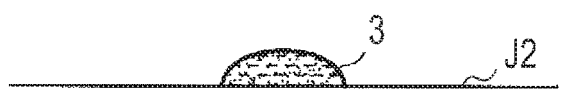
FIG. 18 is a diagram (No. 4) showing the preparation method of a standard sample used in the second embodiment.

As a result, as shown in FIG. 18, the standard sample 3 in which the background 1 and the sample are mixed is prepared.

Since the standard sample 3 thus prepared is in a solidified state, the solid is broken with a needle or the like and dredged on the test subject, or the Teflon sheet J2 is directly rubbed against the test subject, whereby the standard sample 3 is transferred onto the test subject.

According to the technique used in the second embodiment, the standard sample 3 superior in uniformity to the first embodiment can be prepared by a much more convenient technique.

In addition, by first weighing a desired amount of the background 1 and adding dropwise the sample solution 2 to the background 1, a required amount of a standard sample can be prepared with no waste.

Third Embodiment

Next, referring to FIG. 19 to FIG. 21, a preparation method of the standard sample 3 used in the third embodiment of the present invention will be explained.

First, the producer adds a desired amount of the sample solution 2 to a suspension of the background 1 and stirs the mixture.

Figure 19:
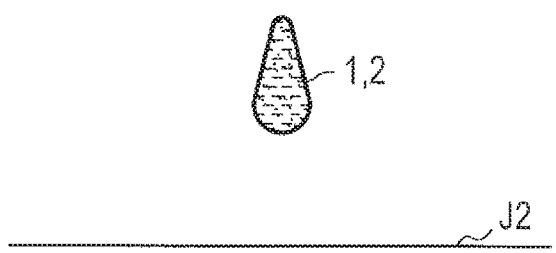
FIG. 19 is a diagram (No. 1) showing a preparation method of a standard sample used in a third embodiment.

Then, as shown in FIG. 19, the mixture of the background 1 and the sample solution 2 is added dropwise onto the Teflon sheet J2.

Figure 20:
FIG. 20 is a diagram (No. 2) showing the preparation method of a standard sample used in the third embodiment.

Then, as shown in FIG. 20, the mixture of the background 1 and the sample solution 2 added dropwise is dried.

Figure 21:
FIG. 21 is a diagram (No. 3) showing the preparation method of a standard sample used in the third embodiment.

When the mixture is dried completely, as shown in FIG. 21, the standard sample 3 in which the background 1 and the sample are mixed prepared on the Teflon sheet J2.

Since the standard sample 3 thus prepared is in a solidified state, the solid is broken with a needle or the like and dredged on the test subject, or the Teflon sheet J2 is directly rubbed against the test subject, whereby the standard sample 3 is transferred onto the test subject.

According to the third embodiment, the standard sample 3 excellent in uniformity can be prepared by a more convenient method than the technique shown in the second embodiment.

Fourth Embodiment

Next, referring to FIG. 22 and FIG. 23, a test method according to the fourth embodiment will be explained. Incidentally, the first to third embodiments show a preparation method of the standard sample 3, but in the fourth and fifth embodiments a test method will be explained.

There has heretofore not been proposed a technique, regarding the gas flow type analysis system w of a type in which particulates attached to a surface of the test subject C are sampled by a gas flow and analyzed as shown in FIGS. 9 to 12, of how to place a standard sample on the test subject C.

Figure 22:
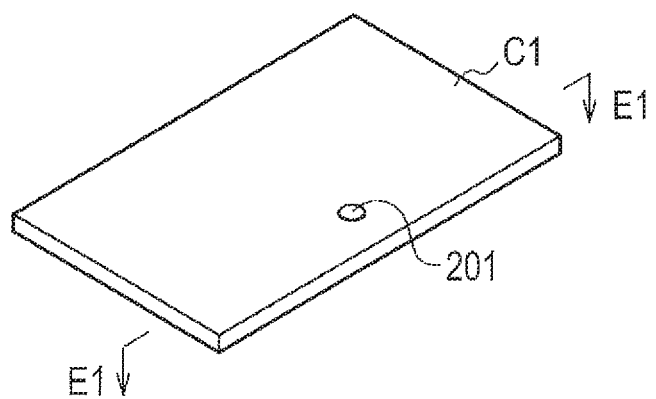
FIG. 22 is a view showing an example of a test subject for evaluation used in a fourth embodiment.

FIG. 22 is a view showing an example of a test subject for evaluation used in the fourth embodiment.

Incidentally, in the fourth embodiment, a case where a card is used as the test subject C1 for evaluation will be explained.

As shown in FIG. 22, the test subject C1 is provided with a recess 201 (depression) to be filled with a desired amount of the background 1.

Figure 23:
FIG. 23 is a cross section of the test subject used in the fourth embodiment.

FIG. 23 is a cross section of the test subject used in the fourth embodiment. FIG. 23 shows an F1-F1 cross section in FIG. 22.

As shown in FIG. 23, the recess 201 is lightly filled with a standard sample 3 prepared by any of techniques of the first to third embodiments and the standard sample 3 is leveled off by a leveling spatula or the like. Then, the test subject C1 in which the recess 201 is filled with the standard sample 3 is set in the gas flow type analysis system w (see FIG. 9) to thereby evaluate the gas flow type analysis system w.

The recess 201 is, for example, of a semi-circular form with a diameter of 1 mm and a depth of 0.2 mm. In the case where the recess 201 having such a size is lightly filled with the test powder (fine) Class 7 Kanto (Japanese) loam for JIS Z8901, the amount of the background 1 is about 60 µg.

According to the fourth embodiment, since the gas flow type analysis system w can be evaluated after accurately measuring the amount of the standard sample 3 prepared by any of the techniques of the first to third embodiments (see FIG. 9), it is possible to perform an evaluation of the gas flow type analysis system w with high accuracy.

Incidentally, in the test subject C1 shown in FIG. 22 and FIG. 23, only one recess 201 is provided, but two or more recesses 201 can be provided therein.

Fifth Embodiment

In the fourth embodiment, the above description is made under the assumption of the test subject C1 being a card, but, aside from a card, a card holder, a cell phone, a pocketbook, a season ticket holder, and various other industrial products can be taken as a test subject for the gas flow type analysis system w (see FIG. 9). Also for such a test subject, when the same configuration (recess 201 (see FIG. 22 and FIG. 23)) as in the fourth embodiment is provided, it is possible to accurately evaluate the performance of the gas flow type analysis system w as shown in FIG. 9 to FIG. 12. However, in the case where the test subject is a hand, an evaluation procedure other than the fourth embodiment is required.

According to the study of the present inventors, it was found that, when a sample for evaluation is prepared, for example, in the same procedure as in the second embodiment, and then. Tee sample for evaluation is attached to a hand and measured by the gas flow type analysis system w of a type in which the attached substance is sampled by a gas flow as shown in FIG. 9 to FIG. 12, the measurement results vary largely depending on the subject person. The cause of the difference is not clear, but it is considered that the difference in perspiration due to the individual variation affects the results.

Figure 24:
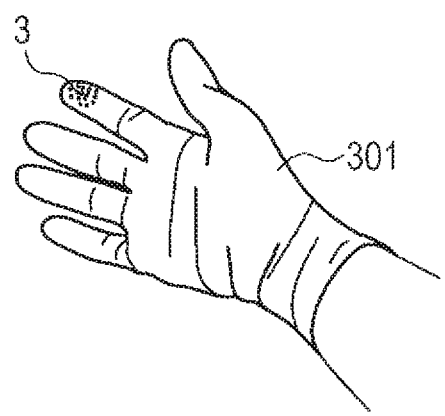
FIG. 24 is a view showing a glove used in a fifth embodiment.
Figure 25:
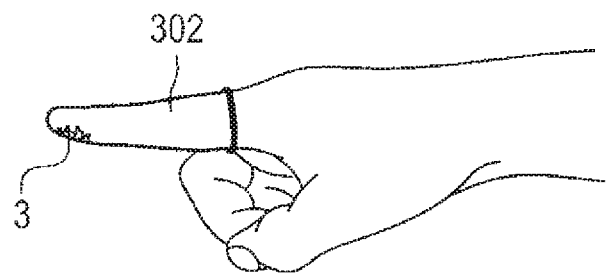
FIG. 25 is a view showing a finger cot used in the fifth embodiment.

Thus, in the fifth embodiment, in order to evaluate the performance of the analysis system w (see FIG. 9) with high reproducibility without causing the individual variation, a part where the standard sample 3 is to be attached is covered with a glove 301 as shown in FIG. 24, a finger cot 302 as shown in FIG. 25, or the like.

A specific example of the procedure is as follows.

The standard sample 3 is first prepared according to any of the techniques shown in the first to third embodiments.

The standard sample thus prepared is attached to a surface of the glove 301 or the finger cot 302 by rubbing the standard sample 3 with a finger wearing the glove 301 or the finger cot 302 as shown in FIG. 24 or FIG. 25, respectively. Then, the hand wearing the glove 301 or the finger cot 302 having the standard sample 3 attached thereto is set in the gas flow type analysis system w (see FIG. 9). In this way, in an evaluation of the gas flow type analysis system w of a type in which a hand is set, it is possible to perform an evaluation with highly reproducibility regardless of the subject person.

The present invention is not limited to the embodiments described above, and a variety of modifications are included. For example, the above embodiments are described in detail comprehensively explain the present invention, and the present invention is not necessarily limited to the embodiment having all the configurations explained above. In addition, a part of a configuration of one embodiment may be replaced with a configuration of another embodiment, and a configuration of one embodiment may be added to a configuration of another embodiment. Furthermore, a part of a configuration of each embodiment can be added to, deleted from, replaced with a configuration of another embodiment.

REFERENCE SIGNS LIST

1: background
2: solution (solution of sample)
2a: sample left on wall
3: standard sample
4: solvent
201: recess
301: glove
302: finger cot
C, C1: test subject
J1: container
J2: Teflon sheet (sheet-like substance)
w: gas flow type analysis system
z: attached substance collection device

The invention claimed is:

1. A method for preparing a standard sample for a gas flow type analysis system, comprising:
    weighing into a container a background, which is particulates, that is possibly attached to a test subject at the time of performing a test by the analysis system for analyzing an attached substance attached to the test subject;
    adding a solution of a sample to the background;
    drying the solution of the sample;
    adding acetone into the container to a level that is higher than a level of the sample deposited on a wall surface of the container; and
    drying the acetone added into the container.

2. A method for preparing a standard sample for a gas flow type analysis system for analyzing an attached substance attached to a test subject, comprising:
    generating a suspension containing a background at a desired concentration;
    adding dropwise the suspension onto a sheet-like substance;
    drying the suspension on the sheet-like substance;
    adding dropwise a solution of a sample to the dried suspension; and
    drying a solution of the suspension and the solution of the sample.

* * * * *